United States Patent [19]

Butter et al.

[11] 4,298,695

[45] Nov. 3, 1981

[54] CONVERSION OF SYNTHESIS GAS WITH IRON-CONTAINING CATALYST

[75] Inventors: Stephen A. Butter; Arthur W. Chester, both of Cherry Hill, N.J.; Albert B. Schwartz, Philadelphia, Pa.

[73] Assignee: Mobil Oil Corporation, New York, N.Y.

[21] Appl. No.: 120,243

[22] Filed: Feb. 11, 1980

Related U.S. Application Data

[63] Continuation-in-part of Ser. No. 970,300, Sep. 18, 1978, abandoned.

[51] Int. Cl.$^3$ .............................................. C07C 1/00
[52] U.S. Cl. .................................................... 518/720
[58] Field of Search .............. 260/449.6 R, 449.6 M, 260/449 R, 449 M; 518/720

[56] References Cited

U.S. PATENT DOCUMENTS 3,553,104  1/1971  Stover et al. ...................... 208/120
4,086,262  4/1978  Chang et al. ............... 260/449 R X

OTHER PUBLICATIONS

Storch et al., The Fischer–Tropsch & Related Syntheses, John Wiley & Sons, New York, 1951, pp. 290–297, 390–391.

*Primary Examiner*—Howard T. Mars
*Attorney, Agent, or Firm*—Charles A. Huggett; Michael G. Gilman; Charles J. Speciale

[57] ABSTRACT

A method is disclosed for the conversion of synthesis gas to a liquid hydrocarbon product having a boiling range of less than 400° F. at a 90% overhead utilizing a novel catalyst prepared from finely divided iron powder or iron oxide. The novel method involves contacting synthesis gas with a single particle catalyst containing iron, a crystalline acidic aluminosilicate zeolite having a silica-to-alumina ratio of at least 12, a pore size greater than about 5 Angstrom units, and a constraint index of about 1 to 12, and a matrix. The catalyst does not contain promoters.

10 Claims, No Drawings

CONVERSION OF SYNTHESIS GAS WITH IRON-CONTAINING CATALYST

CROSS REFERENCE TO RELATED CASES

This application is related to application Ser. No. 970,307, filed Sept. 18, 1978. This application is a continuation-in-part of Ser. No. 970,300, filed Sept. 18, 1978 now abandoned.

BACKGROUND OF THE INVENTION

Field of the Invention

This invention is concerned with an improved process for converting synthesis gas, i.e., mixtures of gaseous carbon oxides with hydrogen or hydrogen donors, to hydrocarbon mixtures.

Processes for the conversion of coal and other hydrocarbons, such as natural gas, to a gaseous mixture consisting essentially of hydrogen and carbon monoxide and/or dioxide are well known. Those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels is given in Encyclopedia of Chemical Technology, Edited by Kirk-Othmer, Second Edition, Volume 10, pages 353-433 (1966), Interscience Publishers, New York, New York.

It is also well known that synthesis gas will undergo conversion to reduction products of carbon monoxide, such as hydrocarbons, at from about 300° F. to about 850° F., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides.

Recently, it has been discovered that the conversion of synthesis gas into valuable products can be greatly enhanced by employing a special type of crystalline aluminosilicate zeolite exemplified by ZSM-5 in admixture with a carbon monoxide reduction catalyst. Thus, for example, in U.S. Pat. No. 4,086,262, there is disclosed a process for the conversion of syngas by passing the same at elevated temperature over a catalyst which comprises an intimate mixture of a Fischer-Tropsch component and a special type of zeolite such as ZSM-5. Said patent points out that the products produced are hydrocarbon mixtures which are useful in the manufacture of heating oil, high octane gasoline, aromatic compounds, and chemical intermediates.

Although U.S. Pat. No. 3,086,262 is primarily directed to multi-particle composite catalysts, i.e. the crystalline aluminosilicate component (one particle) is physically admixed with the Fischer-Tropsch component (another particle), nevertheless, Example 5 of said patent does disclose a single particle iron-containing catalyst in an alumina matrix.

As can well be appreciated, the patent and technical literature relating to the Fischer-Tropsch process, is, indeed, extensive and the various catalysts reported in the prior art have been used by themselves as well as in admixture with catalytically inactive supports such as kieselguhr. Although the reasons for using catalytically inactive supports have varied, nevertheless, it would appear that one reason for using the same was that it resulted in increased surface area of the Fischer-Tropsch component upon which it was deposited or admixed and that it also aided in controlling the heat-requirements of the overall exothermic reactions.

It is also known in the art to admix a Fischer-Tropsch component with a material, such as silica-alumina which is known to be catalytically active for the conversion of hydrocarbons.

In copending application Ser. No. 970,307, filed Sept. 18, 1978, there is disclosed a syngas conversion process utilizing a single particle iron-containing catalyst prepared from a water insoluble iron derivative of an organic compound such as iron oxalate.

DESCRIPTION OF PREFERRED EMBODIMENTS

The novel fluid process of this invention is directed towards an improvement in the process of converting syngas to a very specific product. The product with which the instant invention is concerned is a naphtha having a boiling range of less than 400° F. at a 90% overhead which is defined as a $C_5+$ naphtha with an aromatic content of 5 to 25 weight percent wherein said fraction is at least 50 weight percent of the total hydrocarbons produced. The instant invention is also concerned with obtaining the above-defined product in good yields and good selectivities from the starting syngas material as well as towards the catalyst per se.

The novel process of this invention is carried out by contacting said synthesis gas with either a fixed bed or fluid catalyst which comprises at least three separate components which are present in a single particle as opposed to a mixture of three separate particles. The fluid catalyst of this invention comprises iron, an acidic crystalline aluminosilicate zeolite having a pore size of about 5 Angstrom units, a silica alumina ratio of at least 12, and a constraint index of about 1-12 (preferably ZSM-5) and a matrix material. The crystalline aluminosilicates employed in the novel process of this invention are fully set forth in aforementioned U.S. Pat. No. 4,086,262 which is herein incorporated by reference. The preferred class of zeolites used is exemplified by ZSM-5, ZSM-11, ZSM-12, etc. As has heretofore been stated, the manner in which the iron is introduced into the catalyst is of prime importance.

The matrix portion of the single particle fluid catalyst is not narrowly critical and suitable matrices include silica, alumina, silica-alumina, silica-zirconia, silica-magnesia, etc. One surprising feature of the novel process of this invention is that the catalysts which are employed may be unpromoted and yet they still exhibit high activity with little evident aging, and, in fact, are capable of converting syngas to the olefinic or aromatic naphtha product previously described while producing no more than 30 weight percent of methane plus ethane, based on total hydrocarbons. In fact, the use of promoters, which the prior art found necessary in previous iron-containing catalysts, is definitely not preferred due to the fact that most promoters are alkaline in nature and they have a tendency to migrate to the acidic crystalline aluminosilicate zeolite component and to decrease the activity of the same. Therefore, it would appear that the single particle catalyst of the instant invention represents a significant departure from the teachings of the prior art in that not only are alkaline promoters not necessary for sustained operation but, in fact, are detrimental to the activity of the zeolitic component.

The single particle iron-containing catalyst of this invention can be prepared by adding the appropriate acidic crystalline aluminosilicate previously defined and either finely divided metallic iron or iron oxide to a hydrogel matrix before drying, homogenizing the same, and thereafter forming either fixed bed or fluid catalysts by conventional techniques followed by calcination if metallic iron is used in order to convert the same to iron oxide.

The amount of iron or iron oxide which is added is not narrowly critical and an amount sufficient to produce 2.5 to 20 weight percent and more preferably 2.5 to 10 weight percent expressed as Fe, based on the finished catalyst, is used.

Following the addition of iron powder or powdered iron oxide, the catalyst can be formulated into a fixed bed or a fluid catalyst by conventional techniques.

It is to be understood that methods of making fluidized catalysts containing crystalline aluminosilicate zeolites and siliceous matrices are well known in the art and that no novelty is claimed in this step per se. Thus, for example, a composite of the crystalline aluminosilicate zeolite and a siliceous matrix can be made by admixing an aqueous alkali metal silicate with or without a particulate weighting agent, such as kaolin clay, desirably as a dispersion in water so as to intimately mix the clay particles with the alkali metal silicate. The admixing is conveniently done at room temperature, although, of course, higher or lower temperatures may be employed if desired. The mixture is then heated, generally to a temperature of from 100°-160° F. and acid is added to adjust the pH to from about 8-10. The temperature is maintained for a time of about 1-6 hours or longer. At this point, if a silica-zirconia weight agent (e.g. clay) matrix is desired, a zirconium salt is added, desirably as an aqueous solution thereof. Acid is then added to reduce the pH to about 4-7 and form a silica gel weighting agent or a silica gel-zirconia gel weighting agent slurry, which is then admixed with a slurry of the acidic crystalline aluminosilicate zeolite previously described and the finely divided metallic iron or iron oxide. The resulting composite is then homogenized and then treated with a source of ammonium ions or hydrogen ions in order to reduce the sodium content to a low level which is desirably less than about 0.1% sodium and then spray dried to produce fluid size particles.

As is generally known in fluid catalysts for catalytic cracking, the catalyst additionally includes a weighting agent. The most preferred weighting agent is kaolin clay. Other weighting agents may be substituted in whole or in part for the kaolin clay so long as the weighting agents are not detrimental to the finished catalyst.

The relative proportion of crystalline aluminosilicate zeolite to matrix is not narrowly critical and it can range from about 5-40 weight percent of the matrix.

As has been indicated earlier, the crystalline aluminosilicate zeolite, the iron or iron oxide and the matrix are then thoroughly mixed in a form of an aqueous slurry in order to homogenize the same and thereafter subdivided and dried to form the desired particles. A particularly good method of making microspherical particles (e.g. of particle size of about 1-200 microns) especially suitable for use in the fluidized process of this invention is spray-drying.

The temperature of the air (or other gas) entering the spray drier is ordinarily within the range of 500°-1,000° F. The temperature used will depend on such factors as the quantity of material to be dried and the quality of air used in the drying. The evaporation rate will vary depending on the quantity of air used in the drying. The temperature of the particles which are being dried is generally within the range of 150°-350° F. at the completion of the drying, but preferably 200°-300° F.

The drying may be affected by a process in which the particles to be dried and a hot air stream are moving in the same direction for the entire drying period (concurrent drying) or where the hot stream flows in the opposite direction (countercurrent drying), or by semi-concurrent drying. It is to be understood that spray-drying to form fluidized catalysts is well known in the art and a representative procedure is described in U.S. Pat. No. 3,553,104, the entire contents of which are incorporated by reference.

If metallic iron is used to prepare the catalysts, it is necessary to calcine the same in air or oxygen-containing gas by heating at temperatures ranging from about 250° F. to about 1100° F. for periods of time ranging from about 1 to 24 hours or longer in order to convert the iron to iron oxide ($Fe_2O_3$).

The iron-containing catalysts must be then pretreated prior to use for the conversion of syngas. In this connection, it has been found that the nature of the pretreatment is critical. The catalyst must be pretreated with syngas or with CO prior to use. As opposed to prior art catalysts, the use of hydrogen alone has an adverse effect on catalytic properties and renders the catalyst totally unfit for use. Treatment with syngas or carbon monoxide is conveniently carried out at atmospheric pressure and at temperatures of about 550°-650° F. for periods of time ranging from about ½ hour up to about 24 hours.

The iron powder or iron oxide powder used to prepare the catalysts should have a particle size of from 1 to 200 microns and should be relatively pure. Two forms of iron powder found to be particularly useful are electrolytically reduced iron (which was shown to contain irregularly shaped particles from about 1 to about 30 microns with a portion 100-200 microns in diameter) and submicron iron powder such as that supplied by Pyron Corporation having particles in the 40-90 micron range.

The iron oxide used is preferably $Fe_2O_3$, although other forms of iron oxide can be used provided it is converted to $Fe_2O_3$ prior to the activation with carbon monoxide or syngas previously described.

Powdered metallic iron is preferred over the use of iron oxide.

The acidic crystalline aluminosilicate component of the catalyst is characterized by a pore dimension greater than about 5 Angstroms, i.e. it is capable of sorbing paraffins, and it has a silica-to-alumina ratio of at least 12 and a constraint index within the range of 1 to 12. Zeolite A, for example, with a silica-to-alumina ratio of 2.0 is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The acidic crystalline aluminosilicate component preferably is in the hydrogen form.

The catalysts referred to herein utilize members of a special class of zeolites exhibiting some unusual properties. They are very active even with silica-to-alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention comprise, in combination: a silica-to-alumina ratio of at least about 12; and a structure providing constrained access to the crystalline free space.

The silica-to-alumina ratio referred to may be determined by conventional analysis. This ratio is meant to represent as closely as possible, the ratio in the rigid anionic framework of the zeolite crystal and to exclude aluminum in the binder or in cationic or other form within the channels. Although zeolites with a silica-to-alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of 12-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1,000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
| --- | --- |
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous silica-alumina | 0.6 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint index seems to vary somewhat with severity of operation (conversion). Therefore, it will be appreciated that it may be possible to so select test conditions to establish multiple constraint indexes for a particular given zeolite which may be both inside and outside the above-defined range of 1 to 12.

Thus, it should be understood that the parameter and property "Constraint Index" as such value is used herein as an inclusive rather than an exclusive value. That is, a zeolite when tested by any combination of conditions within the testing definition set forth hereinabove to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-35 and ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is described in U.S. Pat. No. 4,016,245 and ZSM-38 is described in U.S. Pat. No. 4,046,859, both of which are incorporated herein by reference.

The novel process of this invention is carried out at temperatures ranging from about 500° to 600° F. and more preferably from 550° to about 580° F. The novel process of this invention is carried out at gas hourly space velocities (GHSV), ranging from 400 to 20,000 and more desirably from 500 to 6,000, based on fresh feed and total catalyst volume. Hydrogen to carbon oxides ratios can vary from 0.5:1 to 2:1 and more preferably are about 1:1, pressures ranging from 50 to 1,000 psig and more preferably from 150 to 400 psig are employed.

The following examples will illustrate the novel process of this invention.

EXAMPLE 1

A silica-clay hydrogel was prepared by adding 153.2 cc of 97.1% sulfuric acid to a slurry of 698 grams of WP kaolin clay in 32.4 lbs of demineralized water and 2989 grams of Q-Brand sodium silicate at 120° F. After heating the mixture of 140° F. for two hours a solution containing 52.3 grams of aluminum sulfate in 209 cc of water was added, followed by 66.8 grams of sodium zirconium silicate in 648 cc water and the pH adjusted to 4.7 by adding sulfuric acid. After standing overnight the equivalent of 40% HZSM-5 and iron powder (electrolytically reduced iron of about 1-200 microns) in an amount sufficient to provide 5.8 weight percent iron based on total catalyst were added and the resulting gel was homogenized and $NH_4+$ exchanged, washed and dried.

EXAMPLE 2

The process of Example 1 was repeated with the exception that enough iron powder was added to provide a catalyst containing 17.1 weight percent iron.

EXAMPLE 3

The process of Example 1 was repeated with the exception that enough iron powder was added to provide a catalyst containing 14.8 weight percent iron.

EXAMPLE 4

The process of Example 1 was repeated with the exception that submicron iron powder of about 40-90 microns was used in an amount sufficient to obtain a catalyst having an iron content of 9.8 weight percent.

EXAMPLE 5

The process of Example 4 was repeated with the exception that sufficient iron powder was added to obtain a catalyst having an iron content of 16.7 weight percent.

EXAMPLE 6

This example represents an attempt to substitute cobalt for iron in the catalyst composition.

Example 1 was repeated with the exception that submicron cobalt was used in place of the iron. Enough metallic cobalt was used to obtain a catalyst having a cobalt content of 5.0 weight percent.

EXAMPLE 7

Example 7 is provided for comparison since it involves impregnation techniques for incorporating iron as opposed to the iron powder.

The general procedure of Example 1 was repeated with the exception that the metallic iron was omitted during formation of the gel. The gel was dried and then impregnated with $Fe(NO_3)_3 \cdot 9H_2O$ in an amount sufficient to provide a composition containing 14.3 weight percent iron.

The various catalysts were then evaluated for the conversion of synthesis gas (1:1 $CO/H_2$) at 200 psig, a WHSV of about 1 and at temperatures of about 575° F. All catalysts were air calcined at 1000° F. for 3 hours. However, comparison data is presented for some catalysts in both a calcined and uncalcined state. The data presented is that from the second day.

The effect of preconditioning by treatment with either hydrogen or 1:1 mixtures of hydrogen and carbon monoxide at atmospheric pressure for about 18 hours is also shown.

| EXAMPLE | 1 | 1 | 2 |
|---|---|---|---|
| Run Time, Hours | 43 | 18 | 42 |
| WHSV | | | |
| CO Conversion, wt. % | 51.5 | <20 | 87.6 |
| $H_2$ Conversion, wt. % | 57.1 | | 67.1 |
| % wt C Converted to: | | | |
| Hydrocarbon | 64.8 | | 57.4 |
| Product Yield, wt. % | | | |
| HC | 15.5 | | 24.9 |
| $H_2O$ | 9.9 | | 6.8 |
| $H_2$ | 3.0 | | 2.3 |
| CO | 45.2 | | 11.6 |
| $CO_2$ | 26.5 | | 54.4 |
| Hydrocarbon | | Too small | |
| Composition, wt. % | | to | |
| $C_1$ | 17.3 | analyze | 19.3 |
| $C_2$ | 6.3 | | 9.6 |
| $C_3$ | 5.0 | | 5.5 |
| $C_4$ | 13.2 | | 9.6 |
| $C_5$ | 9.9 | | 8.8 |
| $C_{6+}$ | 48.3 | | 47.3 |
| Olefins, wt. % by C No. | | | |
| $C_2=$ | 30.2 | | 6.7 |
| $C_3=$ | 29.0 | | 12.8 |
| $C_4=$ | 19.9 | | 25.2 |
| $C_5=$ | 18.4 | | 33.5 |
| $C_5$ Olefin Distribution, wt. % | | | |
| $C_5=1$ | 2.2 | | 2.1 |
| $2MIC_4=$ | 15.3 | | 16.7 |
| $3MIC_4=$ | 0.7 | | 1.3 |
| $T2C_5=$ | 12.4 | | 12.1 |
| $C_2C_5=$ | 5.8 | | 5.9 |
| $2M2C_4=$ | 63.5 | | 61.8 |
| $C_{6+}$ Aromatics, wt. % | 17.1 | | 8.2 |
| Liq. Prod. 90% Pt., °F. (D-2887) | 366 | | 365 |
| $C_{5+}$ | 58.2 | | 56.1 |

| | -continued | | |
|---|---|---|---|
| Air Calcined | Yes | Yes | Yes |
| Pretreatment | A | B | A |
| EXAMPLE | 3 | 4 | 5 |
| Run Time, Hours | 18 | 18 | 18 |
| WHSV | | | |
| CO Conversion, wt. % | 69.4 | 61.4 | 93.0 |
| $H_2$ Conversion, wt. % | 62.9 | 54.9 | 68.6 |
| % wt C Converted to: | | | |
| Hydrocarbon | 60.9 | 65.5 | 57.0 |
| Product Yield, wt. % | | | |
| HC | 20.6 | 18.6 | 25.0 |
| $H_2O$ | 8.9 | 11.3 | 8.1 |
| $H_2$ | 2.9 | 3.2 | 2.5 |
| CO | 28.2 | 35.8 | 6.5 |
| $CO_2$ | 39.3 | 31.0 | 58.0 |
| Hydrocarbon Composition, wt. % | | | |
| $C_1$ | 17.8 | 15.5 | 17.6 |
| $C_2$ | 8.0 | 5.0 | 6.4 |
| $C_3$ | 4.8 | 4.9 | 4.5 |
| $C_4$ | 9.6 | 12.3 | 9.1 |
| $C_5$ | 9.9 | 10.0 | 10.7 |
| $C_{6+}$ | 49.9 | 52.4 | 51.8 |
| Olefins, wt. % by C No. | | | |
| $C_2=$ | 15.7 | 19.7 | 10.0 |
| $C_3=$ | 16.1 | 0.4 | 19.4 |
| $C_4=$ | 30.4 | 13.1 | 26.3 |
| $C_5=$ | 43.2 | 24.1 | 35.8 |
| $C_5$ Olefin Distribution, wt. % | | | |
| $C_5=1$ | 2.2 | 2.0 | 0.1 |
| $2MIC_4=$ | 17.0 | 16.7 | 17.0 |
| $3MIC_4=$ | 1.4 | 1.1 | 1.4 |
| $T2C_5=$ | 12.8 | 11.9 | 12.2 |
| $C_2C_5=$ | 6.2 | 5.9 | 6.0 |
| $2M2C_4=$ | 60.5 | 62.4 | 61.3 |
| $C_{6+}$ Aromatics, wt. % | 11.7 | 19.8 | 14.4 |
| Liq. Prod. 90% Pt., °F. (D-2887) | 365 | 347 | 366 |
| $C_{5+}$ | 59.8 | 62.4 | 62.5 |
| Air Calcined | Yes | Yes | Yes |
| Pretreatment | A | A | A |
| EXAMPLE | 5 | 6 | 6 |
| Run Time, Hours | | | |
| WHSV | | | |
| CO Conversion, wt. % | 0 | 0 | 0 |
| $H_2$ Conversion, wt. % | | | |
| % wt C Converted to: | | | |
| Hydrocarbon | | | |
| Product Yield, wt. % | | | |
| HC | | | |
| $H_2O$ | | | |
| $H_2$ | | | |
| CO | | | |
| $CO_2$ | | | |
| Hydrocarbon Composition, wt. % | | | |
| $C_1$ | | | |
| $C_2$ | | | |
| $C_3$ | | | |
| $C_4$ | | | |
| $C_5$ | | | |
| $C_{6+}$ | | | |
| Olefins, wt. % by C No. | | | |
| $C_2=$ | | | |
| $C_3=$ | | | |
| $C_4=$ | | | |
| $C_5=$ | | | |
| $C_5$ Olefin Distribution, wt. % | | | |
| $C_5=1$ | | | |
| $2MIC_4=$ | | | |
| $3MIC_4=$ | | | |
| $T2C_5=$ | | | |
| $C_2C_5=$ | | | |
| $2M2C_4=$ | | | |
| $C_{6+}$ Aromatics, wt. % | | | |
| Liq. Prod. 90% Pt., °F. (D-2887) | | | |
| $C_{5+}$ | | | |
| Air Calcined | No | No | No |
| Pretreatment | A | B | A |
| EXAMPLE | | 6 | 7 |
| Run Time, Hours | | | 18 |

| | -continued | |
|---|---|---|
| WHSV | | |
| CO Conversion, wt. % | 0 | 34.8 |
| $H_2$ Conversion, wt. % | | 46.4 |
| % wt C Converted to: | | |
| Hydrocarbon | | 73.3 |
| Product Yield, wt. % | | |
| HC | | 11.9 |
| $H_2O$ | | 10.1 |
| $H_2$ | | 3.8 |
| CO | | 60.6 |
| $CO_2$ | | 13.6 |
| Hydrocarbon Composition, wt. % | | |
| $C_1$ | | 16.6 |
| $C_2$ | | 6.3 |
| $C_3$ | | 4.3 |
| $C_4$ | | 12.3 |
| $C_5$ | | 8.1 |
| $C_{6+}$ | | 52.5 |
| Olefins, wt. % by C No. | | |
| $C_2=$ | | 30.3 |
| $C_3=$ | | 9.8 |
| $C_4=$ | | 30.5 |
| $C_5=$ | | 35.9 |
| $C_5$ Olefin Distribution, wt. % | | |
| $C_5=1$ | | 2.0 |
| $2MIC_4=$ | | 16.4 |
| $3MIC_4=$ | | 1.1 |
| $T2C_5=$ | | 11.8 |
| $C_2C_5=$ | | 5.7 |
| $2M2C_4=$ | | 62.9 |
| $C_{6+}$ Aromatics, wt. % | | 15.4 |
| Liq. Prod. 90% Pt., °F. (D-2887) | | 366 |
| $C_{5+}$ | | 60.6 |
| Air Calcined | Yes | Yes |
| Pretreatment | A | A |

A = CO + $H_2$ at 600–615° F.
B = $H_2$ at 900° F.

From the above table, it can be seen that metallic cobalt was completely inoperative irrespective of calcination or pretreatment (Example 6).

It is also evident that calcination is absolutely necessary when employing metallic iron. Compare uncalcined Example 5 with Examples 1–4.

The nature of pretreatment is also critical. Note that conventional hydrogen pretreatment resulted in poor performance. Compare the results obtained with the catalyst of Example 1 at two different pretreatment procedures.

The Examples also demonstrate the superiority of the catalysts prepared from iron powder as opposed to conventional impregnation techniques. Note that Examples 1 and 4 (iron powder) contained less iron than Example 7 (impregnation) and yet were more active for CO conversion. Example 3 which contained about the same amount of iron (14.8 weight percent) as Example 7 (14.3 weight percent) was almost twice as active.

Finally, the data demonstrate that the submicron iron i.e. 40–90 microns, was more active than the electrolytically reduced iron (1–200 microns). Example 2 had more iron than Example 5, i.e. 17.1, as opposed to 16.7 weight percent, but was not as active.

What is claimed is:

1. A process for converting synthesis gas comprising carbon monoxide and hydrogen to a naphtha having a boiling range of less than 400° F. at a 90% overhead while producing no more than 30 weight percent of methane plus ethane, based on total hydrocarbons, which comprises:

a. contacting said synthesis gas at a temperature of from about 500° to 600° F. and at a pressure of from 50–1000 psig with a catalyst composition prepared by forming a homogenous mixture of either metallic iron powder or iron oxide powder having a particle size no greater than about 200 microns; a hydrogel matrix and an acidic crystalline aluminosilicate zeolite having a silica-to-alumina ratio of at least 12, a pore size greater than about 5 Angstrom units, and a constraint index of about 1 to 12, drying said mixture and treating it with carbon monoxide or synthesis gas mixtures containing carbon monoxide and hydrogen at atmospheric pressure and at temperatures of about 550°–650° F. for periods of time ranging from about ½ hour up to about 24 hours, provided that said dried mixture is calcined in an oxygen-containing gas at temperatures ranging from about 250° F. to about 1100° F. prior to said carbon monoxide treatment when metallic iron is employed to form said mixture and b. obtaining said naphtha in an amount which is at least 50 weight percent of the total hydrocarbons produced.

2. The process of claim 1, wherein said catalyst composition has been spray dried to produce fluidizable particles.

3. The process of claim 1, wherein metallic iron powder is used to prepare said catalyst mixture.

4. The process of claim 2, wherein metallic iron powder is used to prepare said catalyst mixture 5. The process of claim 4, wherein said iron powder is about 10–90 microns.

6. The process of claim 1, wherein said matrix is selected from the group consisting of silica, alumina, silica-alumina, silica-zirconia, and silica magnesia.

7. The process of claim 1, wherein said matrix is a siliceous hydrogel.

8. The process of claim 1, wherein said matrix comprises an alumina hydrogel.

9. The process of claim 1, wherein said matrix comprises a silica-alumina hydrogel.

10. The process of claims 1, 2, 3, 4, or 5, wherein the zeolite is ZSM-5.

* * * * *

UNITED STATES PATENT AND TRADEMARK OFFICE
CERTIFICATE OF CORRECTION

PATENT NO. : 4,298,695

DATED : November 3, 1981

INVENTOR(S) : Stephen A. Butter et al

It is certified that error appears in the above—identified patent and that said Letters Patent is hereby corrected as shown below:

Column 1, line 56, "U.S. Pat. No. 3,086,262" should be --U.S. Pat. No. 4,086,262--

Column 12, line 7, after "mixture" insert a period ---.---

Signed and Sealed this

Eighteenth Day of May 1982

[SEAL]

Attest:

Attesting Officer

GERALD J. MOSSINGHOFF

Commissioner of Patents and Trademarks